United States Patent
Foss et al.

(10) Patent No.: US 10,935,402 B2
(45) Date of Patent: Mar. 2, 2021

(54) FLUID CONTAMINANT DETECTION USING NOISE LEVELS IN MAGNETIC FLOW METER SENSOR SIGNALS

(71) Applicant: Micro Motion, Inc., Boulder, CO (US)

(72) Inventors: Scot Ronald Foss, Eden Prairie, MN (US); Andrew Thomas Kline, Eagan, MN (US)

(73) Assignee: MICRO MOTION, INC., Boulder, CO (US)

( * ) Notice: Subject to any disclaimer, the term of this patent is extended or adjusted under 35 U.S.C. 154(b) by 211 days.

(21) Appl. No.: 16/123,495

(22) Filed: Sep. 6, 2018

(65) Prior Publication Data
US 2020/0080877 A1    Mar. 12, 2020

(51) Int. Cl.
| | |
|---|---|
| *G01N 27/74* | (2006.01) |
| *G01F 1/58* | (2006.01) |
| *G01M 3/26* | (2006.01) |
| *G01N 33/28* | (2006.01) |

(52) U.S. Cl.
CPC ............ *G01F 1/588* (2013.01); *G01M 3/26* (2013.01); *G01N 27/74* (2013.01); *G01N 33/2835* (2013.01); *G01N 33/2841* (2013.01)

(58) Field of Classification Search
CPC ............ G01N 27/74; G01N 33/2835; G01N 33/2841; G01M 3/26; G01F 1/58; G01F 1/60; G01F 1/74; G01F 1/588
See application file for complete search history.

(56) References Cited

U.S. PATENT DOCUMENTS

| | | | | | |
|---|---|---|---|---|---|
| 3,847,020 | A | * | 11/1974 | Jurschak | ........... G01F 1/00 73/861.71 |
| 5,487,310 | A | | 1/1996 | Higuchi | |
| 6,505,517 | B1 | * | 1/2003 | Eryurek | ........... G01F 1/60 702/189 |
| 7,788,046 | B2 | | 8/2010 | Schmalzried et al. | |
| 8,340,920 | B2 | * | 12/2012 | Schrag | ........... G01F 1/58 702/28 |
| 2003/0051557 | A1 | | 3/2003 | Ishikawa et al. | |
| 2008/0250867 | A1 | * | 10/2008 | Schmalzried | ........ G01F 1/60 73/861.11 |
| 2009/0120203 | A1 | | 5/2009 | Schrag et al. | |
| 2017/0261357 | A1 | | 9/2017 | Wang et al. | |

FOREIGN PATENT DOCUMENTS

| | | |
|---|---|---|
| DE | 10 2007 015 368 | 10/2008 |
| JP | 2856521 | 2/1999 |

OTHER PUBLICATIONS

Office Action from Chinese Patent Application No. 201822027709.7, dated Jul. 4, 2019.
Notification of Transmittal of the International Search Report and the Written Opinion of the International Searching Authority, from International Application No. PCT/US2019/037680, dated Sep. 18, 2019.

\* cited by examiner

*Primary Examiner* — Minh N Tang
(74) *Attorney, Agent, or Firm* — Westman, Champlin & Koehler, P.A.

(57) ABSTRACT

A magnetic flow meter includes electrode sensors generating a sensor signal indicative of flow of a liquid through a conduit. A noise identification module identifies a noise level in the sensor signal and a contaminant identification module uses the noise level to determine whether there is a contaminant in the liquid in the conduit.

26 Claims, 20 Drawing Sheets

FLUID CONTAMINANT DETECTION USING NOISE LEVELS IN MAGNETIC FLOW METER SENSOR SIGNALS

BACKGROUND

Oil wells bring fossil-fuels from underground to the surface. In many wells, the output of the well includes a combination of oil, natural gas, water and solid material, such as sand or silt. Separators reside on onshore well pads and offshore platforms and are used to separate the oil and natural gas from each other and from the water and solid debris.

There are many types of density separators but they all function in the same manner by using gravity and an emulsifier layer to separate the constituents of the well output. In particular, the separators slow the fluid flow to allow heavier sand and water to separate from the oil. The water and solid material pass through the emulsifier layer while the oil remains on top of the emulsifier layer. A space is provided above the oil that allows the natural gas to separate from the oil. One or more mist converters may be provided to collect oil droplets that may be suspended in the natural gas.

Separators include an inflow pipe that brings the output of the well into the separator, a natural gas output pipe, an oil output pipe and a water output pipe. If the oil level or water level drops too low, it is possible for natural gas to flow into the oil output pipe or the water output pipe. In addition, it is possible for oil or sand to enter the water output pipe. To prevent this, some separators place valves on the oil output pipe and the water output pipe that are designed to close when the oil level or the water level is too low. These valves, however, are susceptible to sticking due to sand and other debris present in the inflow to the separator. It would be useful to determine if gas, oil or sand is present in the water flow and to determine if gas is present in the oil flow.

SUMMARY

A magnetic flow meter includes electrode sensors generating a sensor signal indicative of flow of a liquid through a conduit. A noise identification module identifies a noise level in the sensor signal and a contaminant identification module uses the noise level to determine whether there is a contaminant in the liquid in the conduit.

In accordance with a further embodiment, a drive signal is applied to generate a magnetic field in a conduit carrying a liquid. A sensor signal is received from electrodes positioned along the conduit and a noise level in the sensor signal is determined. The noise level is used to determine if the liquid contains a contaminant.

In accordance with a still further embodiment, a process transmitter includes a magnetic coil and electrode sensors configured to generate a sensor signal. A noise identification module is configured to determine a level of noise in the sensor signal and a contaminant identification module is configured to identify that a liquid contains a contaminant based on the determined level of noise.

This Summary and the Abstract are provided to introduce a selection of concepts in a simplified form that are further described below in the Detailed Description. The Summary and the Abstract are not intended to identify key features or essential features of the claimed subject matter, nor are they intended to be used as an aid in determining the scope of the claimed subject matter.

DETAILED DESCRIPTION OF ILLUSTRATIVE EMBODIMENTS

Embodiments described below provide process transmitters that detect when a conductive liquid carried by a conduit contains a contaminant such as a gas, another liquid or particulates, such as sand, for example. The process transmitters make these determinations by monitoring the noise level in a magnetic flow meter's sensor signal. The present inventors have discovered that as the amount of a contaminant in a liquid increases, the noise level of the magnetic flow meter's sensor signal increases.

Figure 1:
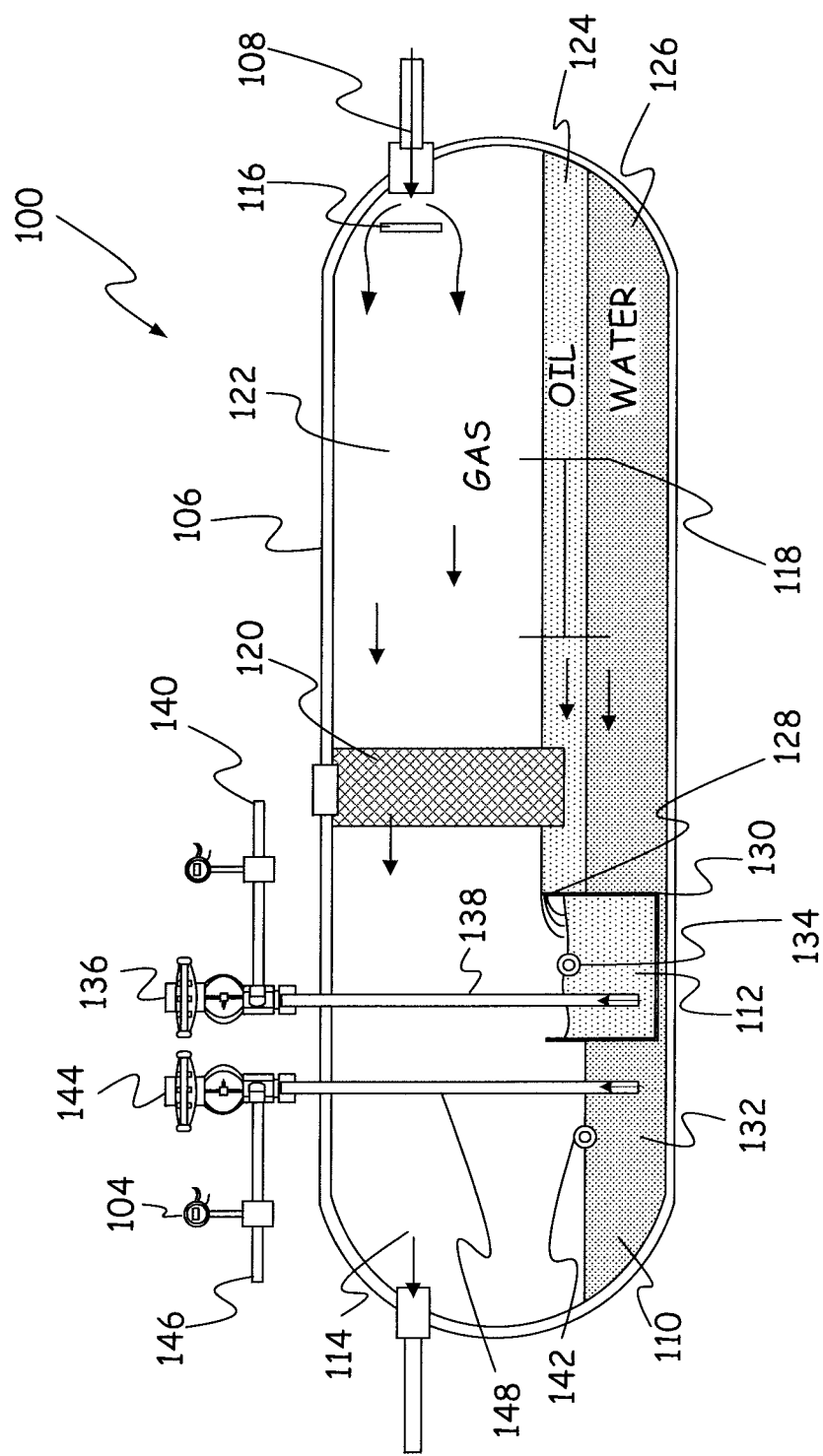
FIG. 1 is a sectional view of a separator.

FIG. 1 provides an example environment 100 in which flow meter 104 of the various embodiments may be utilized. Environment 100 includes a separator tank 106 that is able to separate an inflow 108 into various constituents including water 110, oil 112, and gas 114. Inflow 108 may be from a well head, in some embodiments.

Separator tank 106 includes an inlet baffle 116 and a quieting baffle 118 that are used to reduce the velocity of inflow 108 to allow the constituents of inflow 108 to separate from each other to form a gas layer 122, an oil layer 124 and a water layer 126. A mist pad 120 collects water and oil droplets present in gas layer 122 and causes the collected oil and water to drop into oil layer 124 and water layer 126. Oil layer 124 and water layer 126 flow toward a weir 128 that separates oil layer 124 from water layer 126. In particular, oil layer 124 flows over the top of weir 128 into an oil chamber 130. Water layer 126 flows under oil chamber 130 and into a water chamber 132.

The level of oil in oil chamber 130 is controlled by a liquid level controller 134 and a valve 136. As liquid level controller 134 drops, valve 136 is closed to prevent fluid from flowing through valve 136. Examples of liquid level controller 134 include a mechanical controller, a pneumatic controller, and an electronic controller. When operating properly, liquid level controller 134 should completely close valve 136 when the oil level drops below the intake of a downcomer 138 thereby preventing gas 114 from flowing through an output oil conduit 140. Preventing gas from flowing through conduit 140 is important since such gas is valuable and can be dangerous if not handled properly.

The level of water in water chamber 132 is controlled by liquid level controller 142 and valve 144. As the water level in water chamber 132 drops, liquid level controller 142 closes valve 144 to prevent fluids from flowing through output water conduit 146. Liquid level controller 142 may be a mechanical controller, a pneumatic controller, or an electronic controller. By closing valve 144, liquid level controller 142 prevents gas 114 from flowing through conduit 146 when the water 110 in chamber 132 drops below an intake of a downcomer 148. This prevents gas from entering a water storage tank thereby preventing the loss of valuable gas and preventing explosive gases from developing within the water storage tank.

For various reasons, it is possible for entrained gas and/or sand to occasionally flow through oil conduit 140 or water conduit 146 and it is possible for oil to flow through water conduit 146. In the embodiments described below, flow meter 104 detects when a contaminant such as gas, oil or sand is flowing in water conduit 146. Upon detecting that a contaminant is present in the conduit, flow meter 104 can provide an alert message and/or an indication of the amount of contaminant that is in the conduit.

Figure 2:
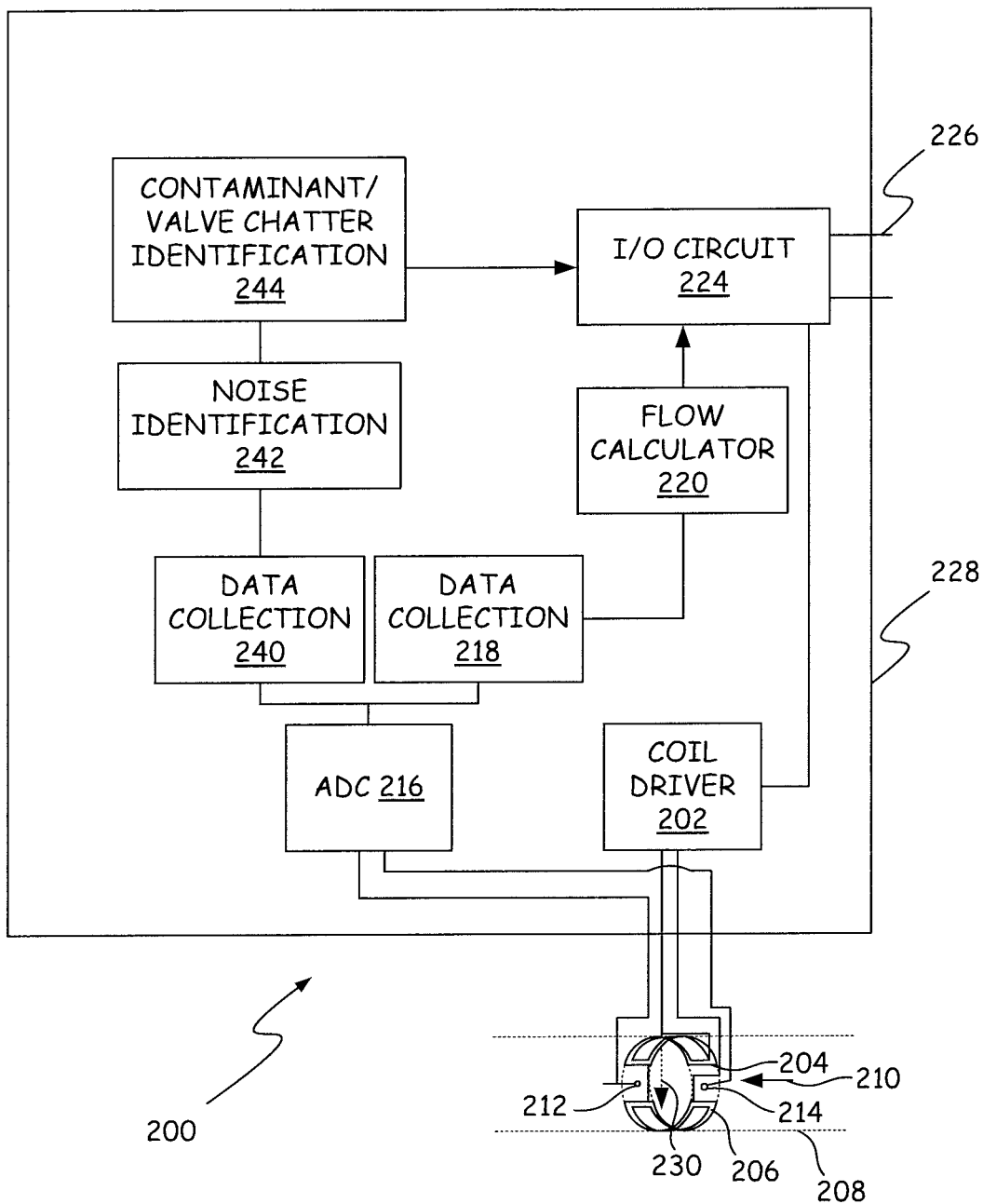
FIG. 2 is a block diagram of a flow meter in accordance with one embodiment.

FIG. 2 provides a schematic diagram of a process transmitter in the form of a magnetic flow meter 200, which is an example of flow meter 104, in accordance with the various embodiments. Magnetic flow meter 200 includes a coil driver 202, which drives electrical current through two coils 204 and 206 positioned on opposite sides of a conduit 208. The current in coils 204 and 206 generates a magnetic field 230 that passes through conduit 208. In accordance with most embodiments, the current in coils 204 and 206 is periodically reversed causing the direction of magnetic field 230 to alternate between extending from coil 204 to coil 206 to extending from coil 206 to coil 204.

Conduit 208 carries a conductive liquid that moves through conduit 208 in a flow direction 210. Polar molecules or charged molecules and atoms within the liquid experience a force that is orthogonal to magnetic field 230 due to their movement through magnetic field 230 in flow direction 210. In particular, positively charged molecules and atoms move in one direction and negatively charged molecules and atoms in an opposite direction. Polar molecules align such that the positive end of the molecules all point in one direction and the negative end of the molecules point in the opposite direction. When the direction of the magnetic field changes, the direction that the charged molecules and atoms move and the orientation of polar molecules switches. This results in an alternating voltage between two electrodes or electrode sensors 212 and 214 that are positioned along a line that is orthogonal to the direction of the magnetic field in the conduit. The magnitude of the voltage is affected by the flow rate of the liquid with faster flow rates resulting in larger voltages.

Electrodes 212 and 214 are connected to an analog-to-digital convertor 216 in a housing 228. Analog-to-digital convertor 216 samples the analog voltage between electrodes 212 and 214 to produce a series of digital samples for a data collection module 218. Data collection module 218 selectively stores some or all of the digital samples for use by a flow calculator 220, which uses the magnitude of the digital samples to estimate a flow rate for the liquid. This flow rate is periodically provided to an input/output circuit 224, which transmits the flow rate to a control room along a communication channel, such as a two-wire process loop 226.

Figure 3:
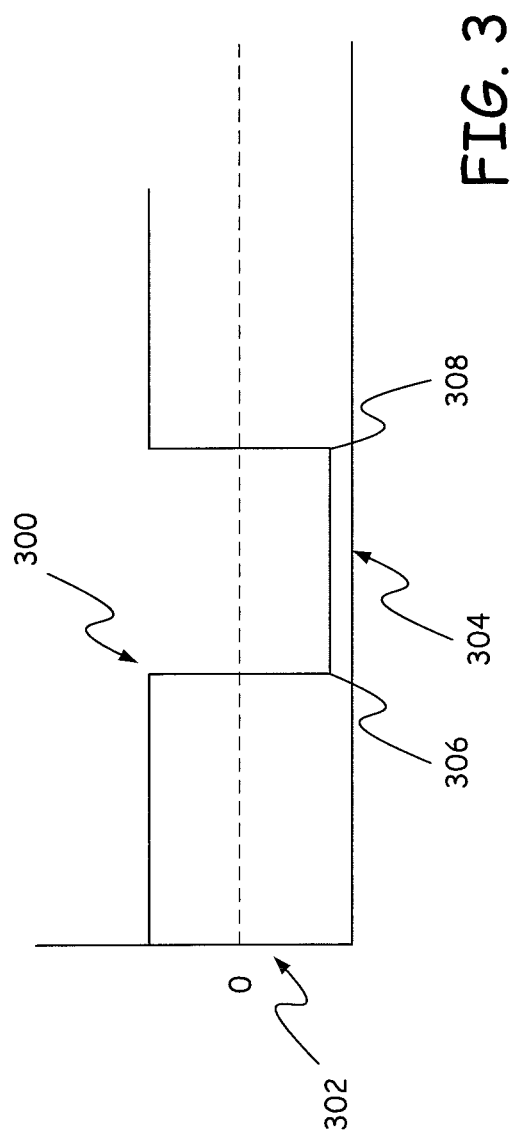
FIG. 3 is a graph of a drive signal for a magnetic flow meter.

FIG. 3 provides a graph 300 of a square wave drive signal that is applied to coils 204 and 206 to generate the magnetic field in accordance with one embodiment. In FIG. 3, the magnitude of the current is shown along vertical axis 302 and time is shown along horizontal axis 304. As shown in FIG. 3, the current alternates between a positive and a negative current of the same magnitude. In accordance with other embodiments, the drive signal is a sine wave or a multi-step pulsed DC wave such as a 75 Hz square wave superimposed on a 5 Hz square wave, for example.

Figure 4:
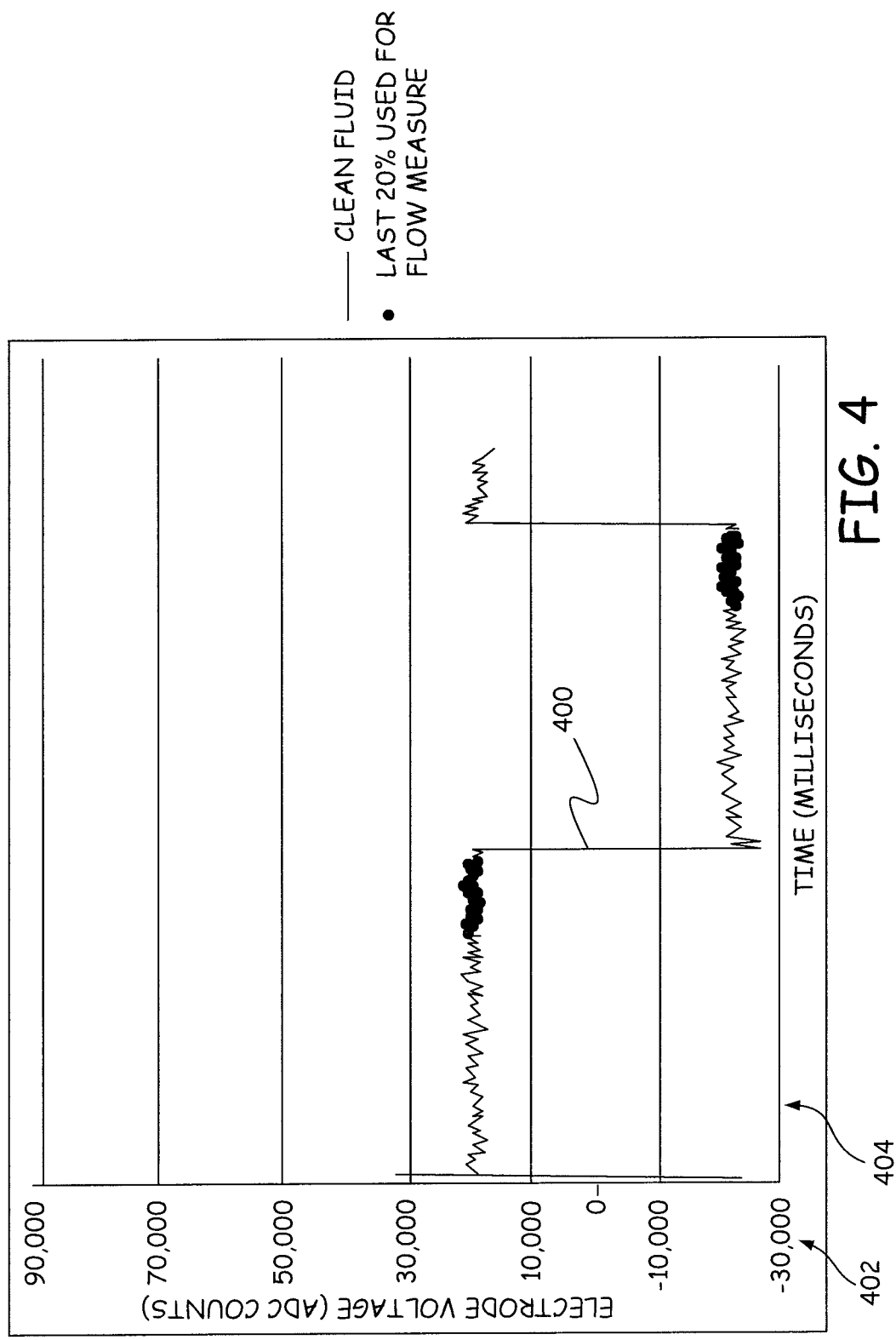
FIG. 4 is a graph of a magnetic flow meter sensor signal in response to the drive signal of FIG. 3 for a liquid that does not contain a contaminant.

FIG. 4 provides a graph 400 of a sensor signal generated between electrodes 212 and 214 when a fluid without a contaminant is flowing through conduit 208 and drive signal 300 is applied to coils 204 and 206. In FIG. 4, the voltage between electrodes 212 and 214 is shown on vertical axis 402 in terms of counts generated by analog-to-digital convertor 216. Time is shown along horizontal axis 404. As shown in FIG. 4, the voltage alternates between positive and negative values of similar magnitudes and is relatively stable at each positive and negative value.

Figure 5:
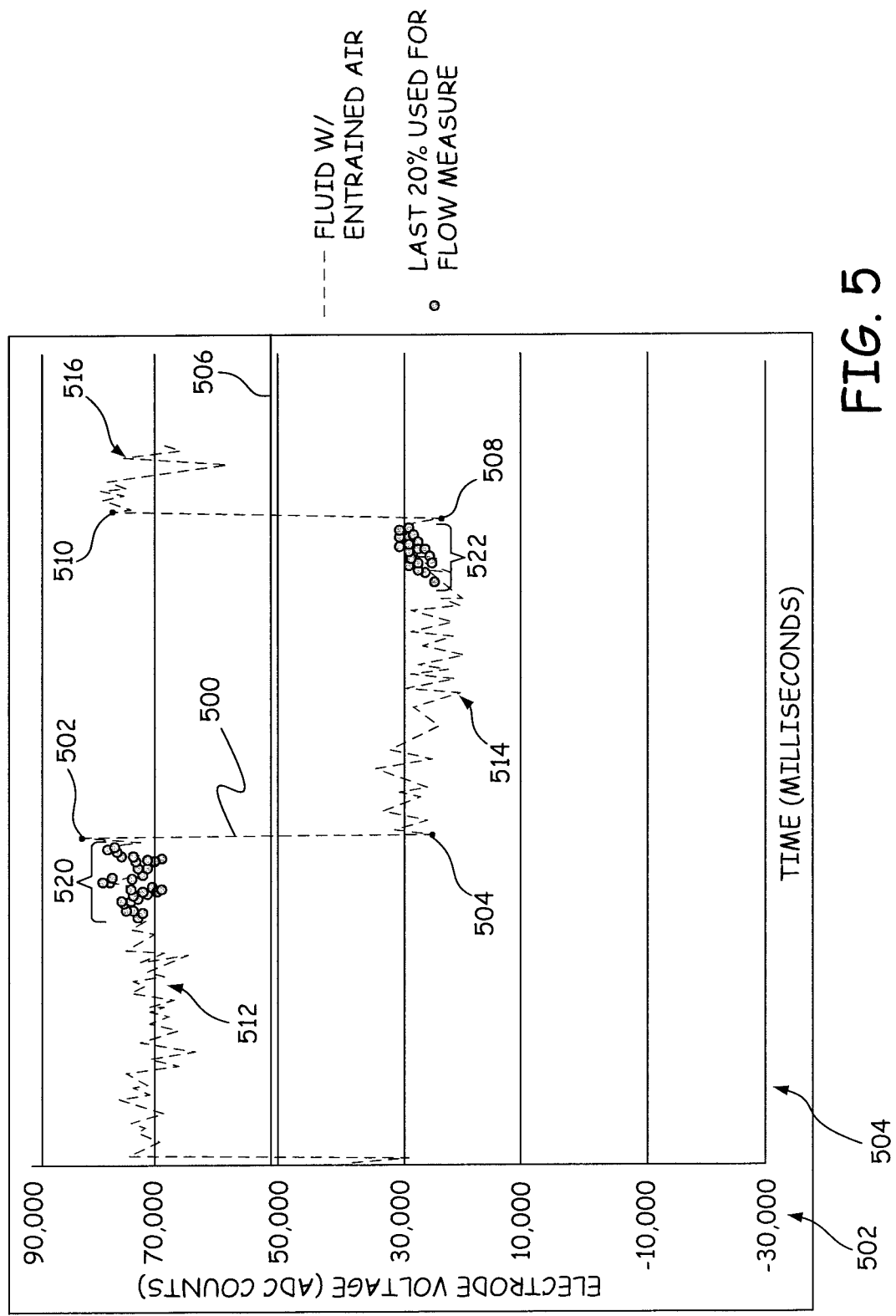
FIG. 5 is a graph of a magnetic flow meter sensor signal in response to the drive signal of FIG. 3 for a liquid containing a contaminant.

FIG. 5 provides a graph 500 of a sensor signal generated between electrodes 212 and 214 when a contaminant is present in the fluid and drive signal 300 is applied to coils 204 and 206. In FIG. 5, the voltage between electrodes 212 and 214 is shown on vertical axis 502 in terms of counts generated by analog-to-digital convertor 216 and time is shown along horizontal axis 504. In addition, the contaminant causes variations in the sensed voltage during the steady-state portions of drive signal 300. The present inventors refer to these variations in the voltage as noise in the sensor signal.

Figure 6:
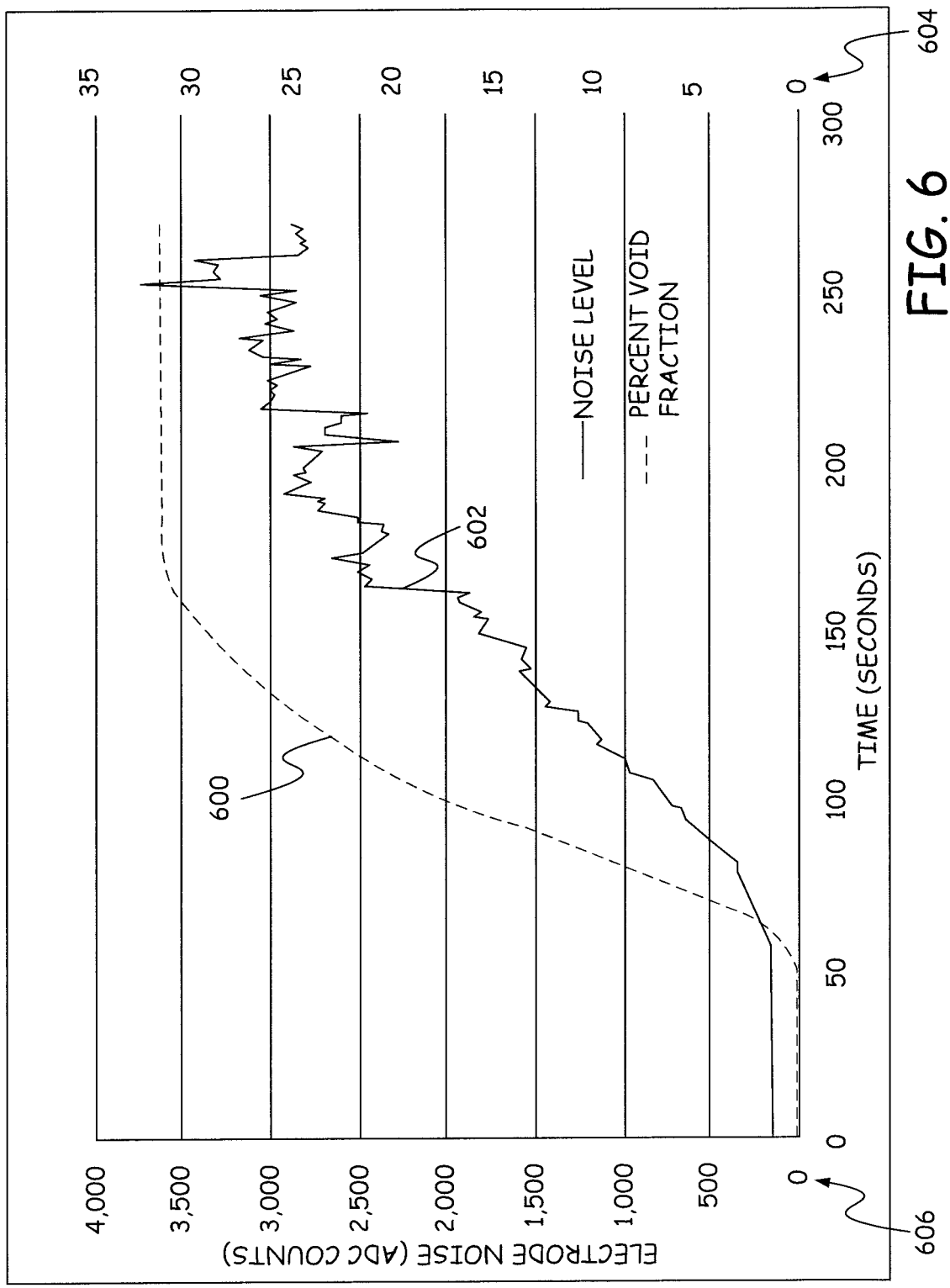
FIG. 6 is a graph of the noise level in the magnetic flow meter sensor signal as a function of the gas void fraction in the liquid.

As discussed further below, the present inventors have developed several techniques for quantifying such noise in the sensor signal of a magnetic flow meter. Using one such technique, the inventors have discovered that the magnitude of the noise is correlated with the amount of a contaminant in a liquid. For example, FIG. 6 provides graphs 600 and 602 showing the correlation between gas void fractions in a liquid and noise levels in a sensor signal. Specifically, graph 600 shows a change in the gas void fraction over time during an experiment, with axis 604 showing the gas void fraction as a percentage of a volume in the conduit. Graph 602 shows the magnitude of the noise in the sensor signal formed during the change in gas void fraction shown in graph 600, with the magnitude of the noise depicted on vertical axis 606. In FIG. 6, it can be seen that soon after the gas void fraction begins to increase, the magnitude of the noise in the sensor signal also increases.

To identify the magnitude of the noise in the sensor signal, the digital values output by analog-to-digital converter 216 are provided to a data collection module 240, which selectively samples and filters the digital values to produce a set of digital values for a noise identification module 242. Noise identification module 242 uses the digital values to identify a sequence of noise values, representing the magnitude of the noise in each of a set of time periods or sections of the sensor signal. The sequence of noise values is provided to a contaminant/valve chatter identification module 244, which filters the sequence of noise values to remove spikes in the noise and uses the filtered noise values to determine if the liquid contains a contaminant or if a valve in the process system is experiencing valve chatter. If the filtered noise values indicate that the liquid contains a contaminant, contaminant/valve chatter identification module 244 optionally provides an estimate of the amount of contaminant in the liquid. When the liquid contains a contaminant or valve chatter is present, contaminant/valve chatter identification module 244 sends an alert through I/O circuit 224 and communication channel 226 indicating the contaminant and optionally the estimated amount of the contaminant.

Figure 7:
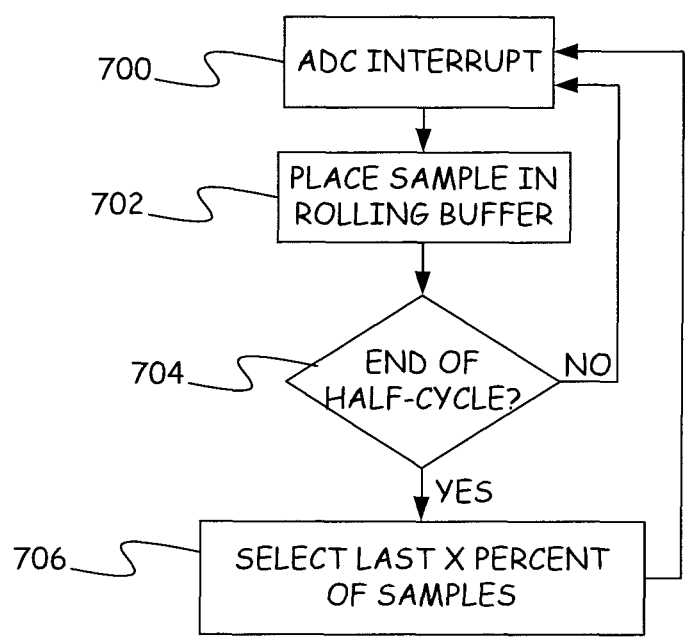
FIG. 7 is a flow diagram of a method of collecting data in accordance with one embodiment.
Figure 8:
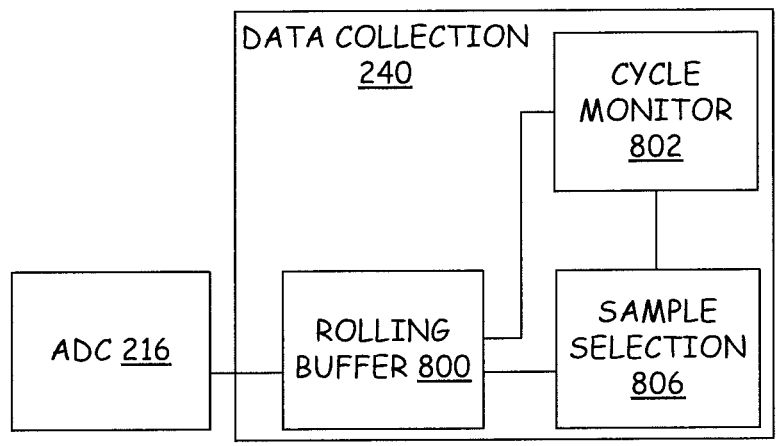
FIG. 8 is a block diagram of elements used in the method of FIG. 7.

FIG. 7 provides a flow diagram of a method implemented by data collection module 240 in accordance with one embodiment. FIG. 8 provides a block diagram of elements used in the method of FIG. 7. In step 700 of FIG. 7, analog-to-digital convertor 216 issues an interrupt signal indicating that analog-to-digital convertor 216 has a new digital sample of the sensor signal. In response to the interrupt, the digital sample output by analog-to-digital convertor 216 is stored in a rolling or circular buffer 800 at step 702. At step 704, a cycle monitor 802 determines if an end of a half-cycle of the drive signal has been reached, where the end of a half-cycle is the point where the drive signal changes polarity. For example, time points 306 and 308 of FIG. 3 each mark the end of a half-cycle in drive signal 300. In accordance with one embodiment, cycle monitor 802 determines if the end of a half-cycle has been reached by comparing the polarity of the drive signal to the polarity determined at a previous time point to see if the polarity has changed. In accordance with other embodiments, the end of the half-cycle is determined by comparing the latest output value from analog-to-digital convertor 216 and a previous output of analog-to-digital convertor 216 to an average of the output values from analog-to-digital converter 216. If one of the values is greater than the average and the other is less than the average, the latest output value is considered to be part of the next half-cycle and the previous output value is considered to the last value in the previous half-cycle. For example, in FIG. 5, line 506 represents the average of the output values from analog-to-digital convertor 216. Sample 502 is shown to be at the end of a half-cycle 512 and is greater than average 506 while sample 504, the sample immediately after sample 502, is shown to be at the beginning of a next half-cycle 514 and is less than average 506. Similarly, sample 508 is shown to be at the end of half-cycle 514 and is less than average 506 while sample 510, which is immediately after sample 508, is shown to be at the beginning of the next half-cycle 516 and is greater than average 506.

If the end of the half-cycle has not been reached at step 704, the process returns to step 700 to await another interrupt from analog-to-digital convertor 216. When the end of the half-cycle has been reached, a sample selection module 806 is triggered to select a percentage of the samples generated during the last half-cycle at step 706. In accordance with one embodiment, the last twenty percent of the samples in the half-cycle are selected. For example, in FIG. 5 the set of samples 520 at the end of half-cycle 512 are selected during a first pass through step 706 and the set of samples 522 at the end of half-cycle 514 are selected during the next pass through step 706. This ensures that the drive signal on the coils and the sensor signal have settled after the previous switch in polarity of the drive signal before using the samples to detect noise in the sensor signal. Although twenty percent of the samples have been used in one embodiment, in other embodiments other percentages are used. The selection of the samples in step 706 is a selection of a portion of the sensor signal for determining a noise level and separate noise levels are determined for each portion of the sensor signal selected with each execution of step 706.

In the embodiment of FIG. 7 a square wave is used as the drive signal. In embodiments where a multi-step pulsed DC wave is used as the drive signal, samples for the last 20% of each half-cycle of the higher-frequency square wave are selected by sample selection module 806. (for example, the 75 Hz square wave when a 75 Hz square wave is superimposed on a 5 Hz square wave to form the pulsed DC wave). In embodiments where the drive signal is a sine wave, a high pass filter is used to by sample selection module 806 to select a subset of the samples for measuring noise.

Figure 10:
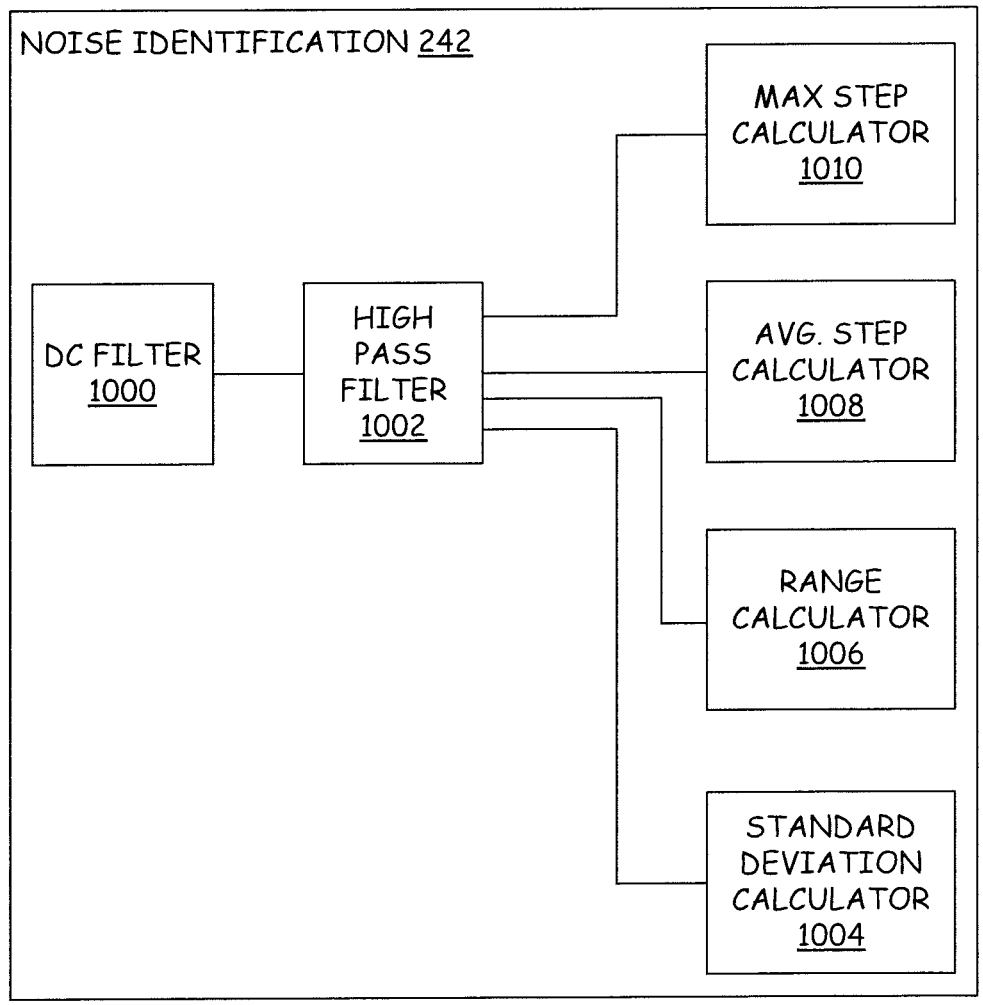
FIG. 10 is a block diagram of elements used in the method of FIG. 9.
Figure 9:
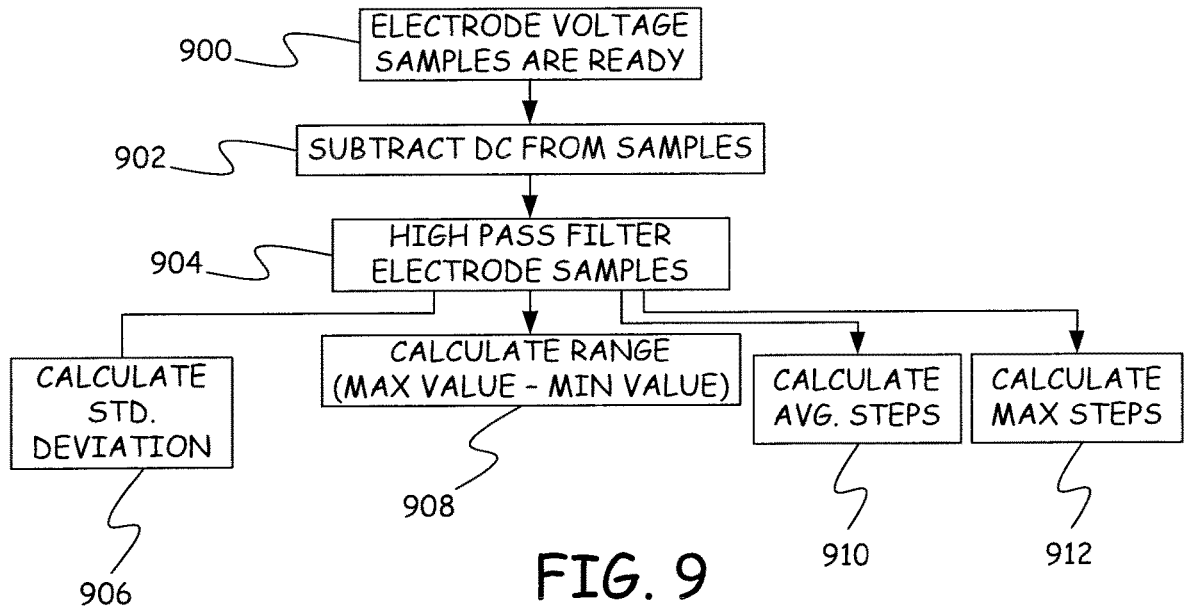
FIG. 9 is a flow diagram of a method of identifying noise levels in a magnetic flow meter sensor signal in accordance with one embodiment.

The selected samples are then processed in noise identification module 242 using the method of FIG. 9 and the elements in the block diagram of FIG. 10 to identify the level of noise in the selected samples. At step 900, the samples selected by data collection 240 are ready to be processed. At step 902, the samples are applied to a DC filter 1000, which subtracts a DC value from the samples. In accordance with one embodiment, the DC value is an average of the selected samples. In step 904, the DC filtered samples are applied to a high-pass filter 1002, which removes low frequency signals common to sensor signals generated from pure liquids that do not contain a contaminant.

After the filtering, the level of noise in the filtered signal can be determined using one or more of a standard deviation calculator 1004 in step 906, a range calculator 1006 in step 908, an average movement per step calculator 1008 in step 910 and/or a maximum movement per step calculator 1010 in step 912. Standard deviation calculator 1004 determines the standard deviation of the filtered samples and sets the noise level to the standard deviation. Range calculator 1006 determines the difference between the largest filtered sample and the smallest filtered sample in the set of samples selected for the half-cycle and sets the noise level to the difference. Average movement per step calculator 1008 determines the average difference between successive filtered samples in the set of samples selected for the half-cycle and sets the noise level to this average difference. Max movement per step calculator 1010 determines the largest difference between successive filtered samples in the set of samples selected for the half-cycle and sets the noise level to this largest difference. In some embodiments, two or more of these noise levels are combined by, for example, averaging the two or more noise levels together.

Figure 11:
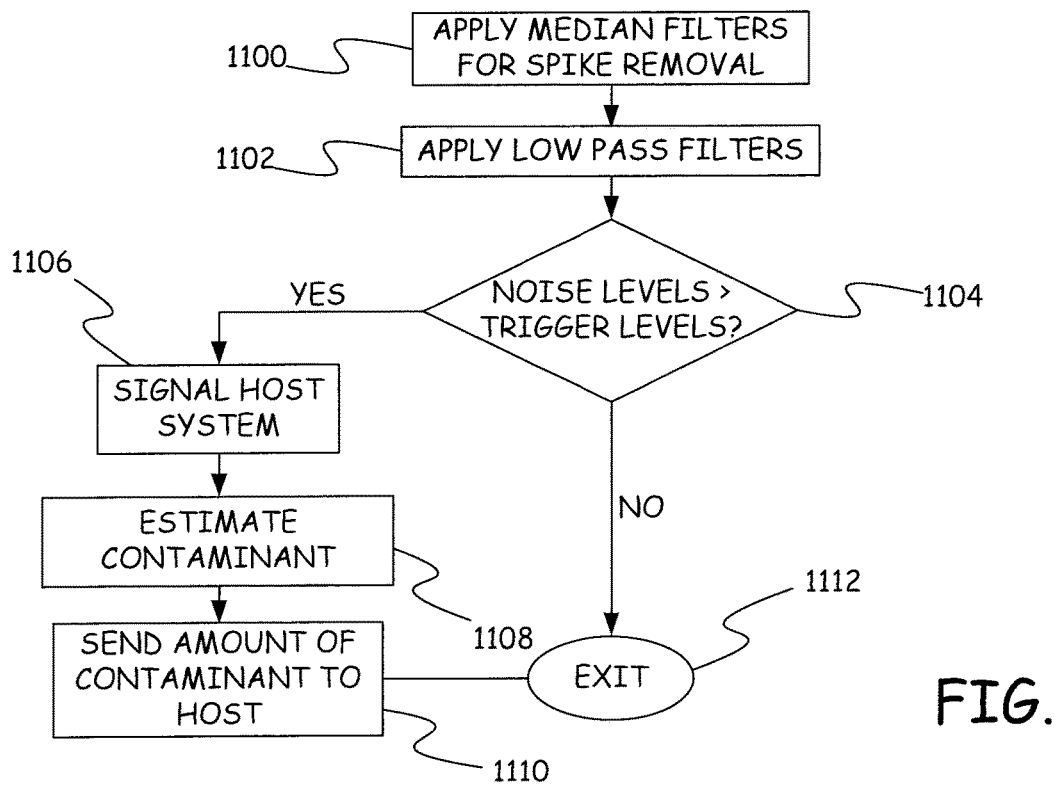
FIG. 11 is a flow diagram of a method of identifying a contaminant using noise levels in accordance with one embodiment.
Figure 12:
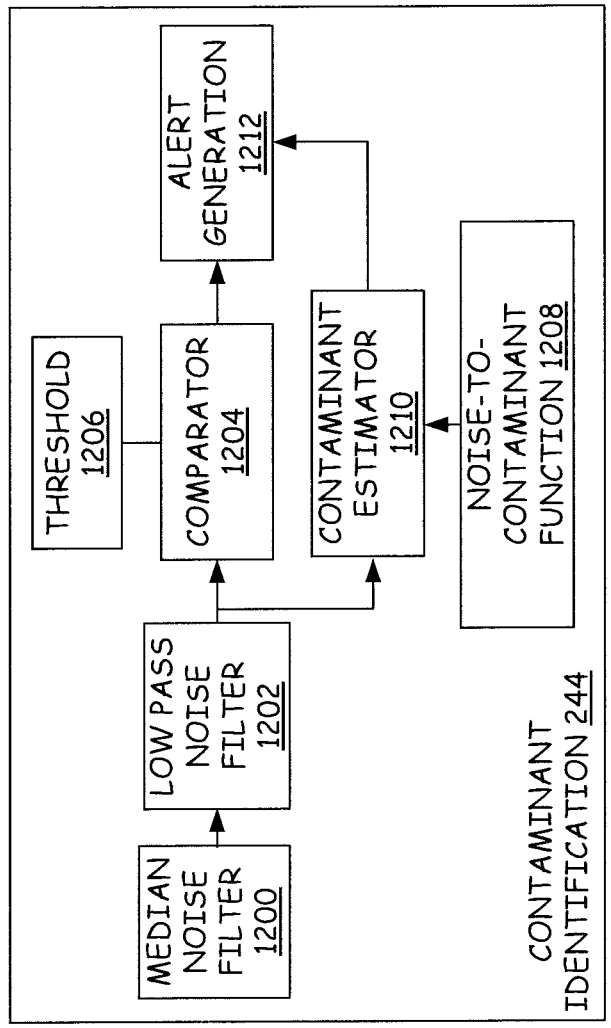
FIG. 12 is a block diagram of elements used in the method of FIG. 11.

The noise levels for each half-cycle are provided to contaminant identification module 244. FIG. 11 provides a flow diagram of a method of identifying a contaminant for the noise levels in accordance with one embodiment. FIG. 12 provides a block diagram of elements used in the method of FIG. 11.

In step 1100 of FIG. 11, the noise levels are applied to a median filter 1200 which forms a window of successive noise levels, such as four successive noise levels, and selects the median of those noise levels as the noise level for the window. At step 1102, the noise levels output by median filter 1200 are applied to a low pass filter 1202 to remove high-frequency noise. At step 1104, the filtered noise levels are applied to a comparator 1204, which compares the filtered noise levels to a threshold 1206. If the filtered noise level does not exceed the threshold, the process of FIG. 11 ends at step 1112. If the filtered noise levels exceed threshold 1206 at step 1104, an alert is sent by alert generation 1212 to a host system through I/O circuit 224 and communication channel 226 at step 1106. Alternatively or additionally, the filtered noise levels are applied to a contaminant estimator 1210, which estimates the amount of contaminant in the liquid using a noise-to-contaminant function 1208 at step 1108. Noise-to-contaminant function 1208 describes the relationship between the filtered noise levels and the amount of contaminant in the liquid and can be determined from experimental data. For example, contaminant estimator 1210 can estimate an amount of gas in a liquid, an amount of oil in a liquid and/or an amount of solid particles in a liquid At step 1110, contaminant estimator 248 sends the amount of contaminant in the liquid to alert generation 1212, which forwards the amount of contaminant to the host through I/O circuit 224 and communication channel 226. In accordance with one embodiment, a single alert is sent by alert generation 1212 to convey that the liquid contains a contaminant and the amount of the contaminant in the liquid.

Figure 13:
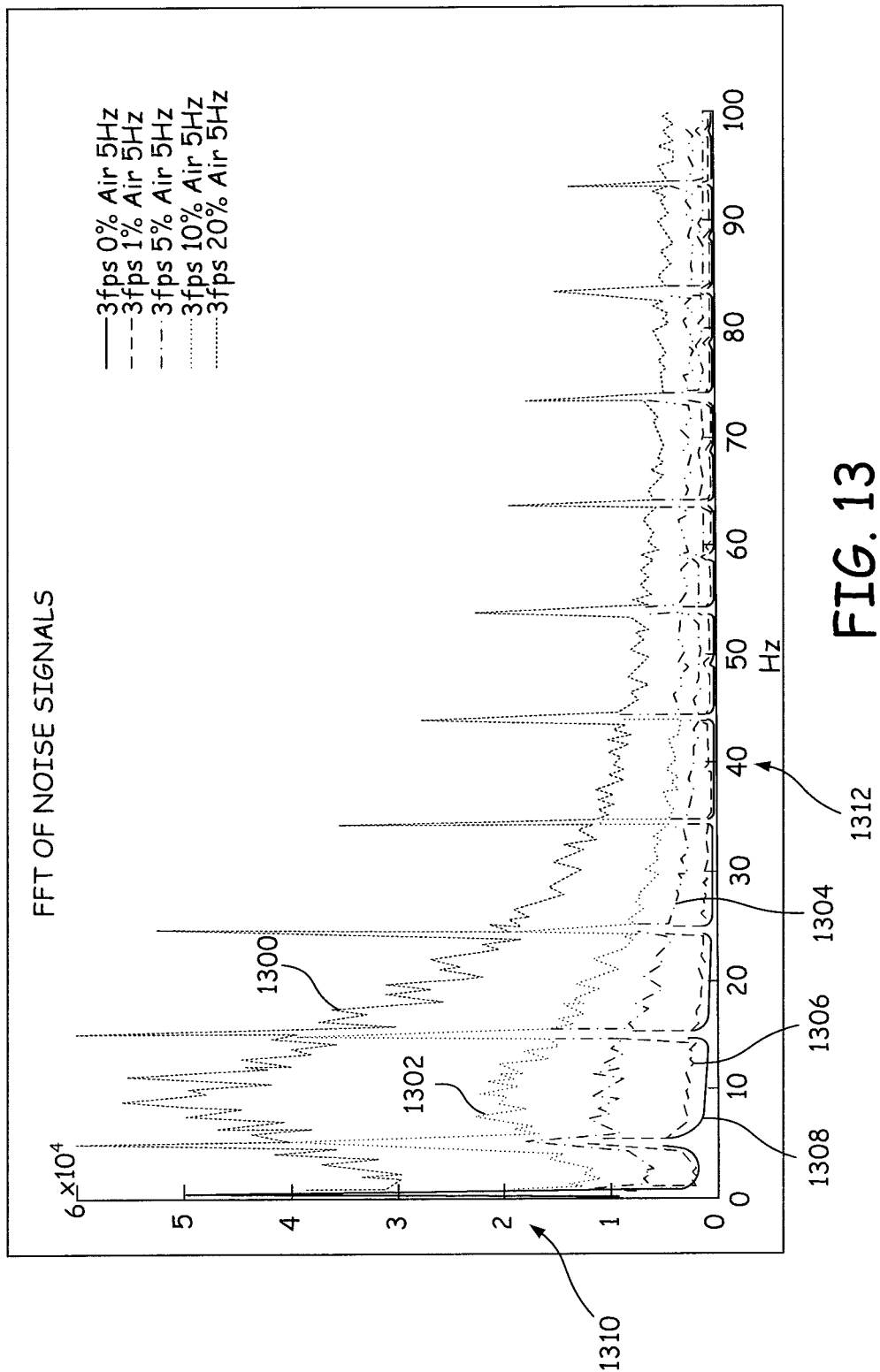
FIG. 13 provides graphs of Fast Fourier Transforms of magnetic flow meter sensor signals for different percentages of gas void fraction.

In accordance with a second embodiment, data collection 240 and noise identification 242 identify a noise level in the sensor signal using a frequency-domain analysis of the sensor signal. FIG. 13 shows graphs 1300, 1302, 1304, 1306, and 1308 of a Fast Fourier Transform of sensor signals from a magnetic flow meter generated from a liquid flowing at 3 feet per second and containing respective amounts of gas void fractions of 20%, 10%, 5%, 1% and 0%. In FIG. 13, the magnitude of the signal is shown along vertical axis 1310 and frequency is shown along horizontal axis 1312. As shown in FIG. 13, as the gas void fraction increases, the magnitude of the sensor signal increases across all frequencies.

Figure 14:
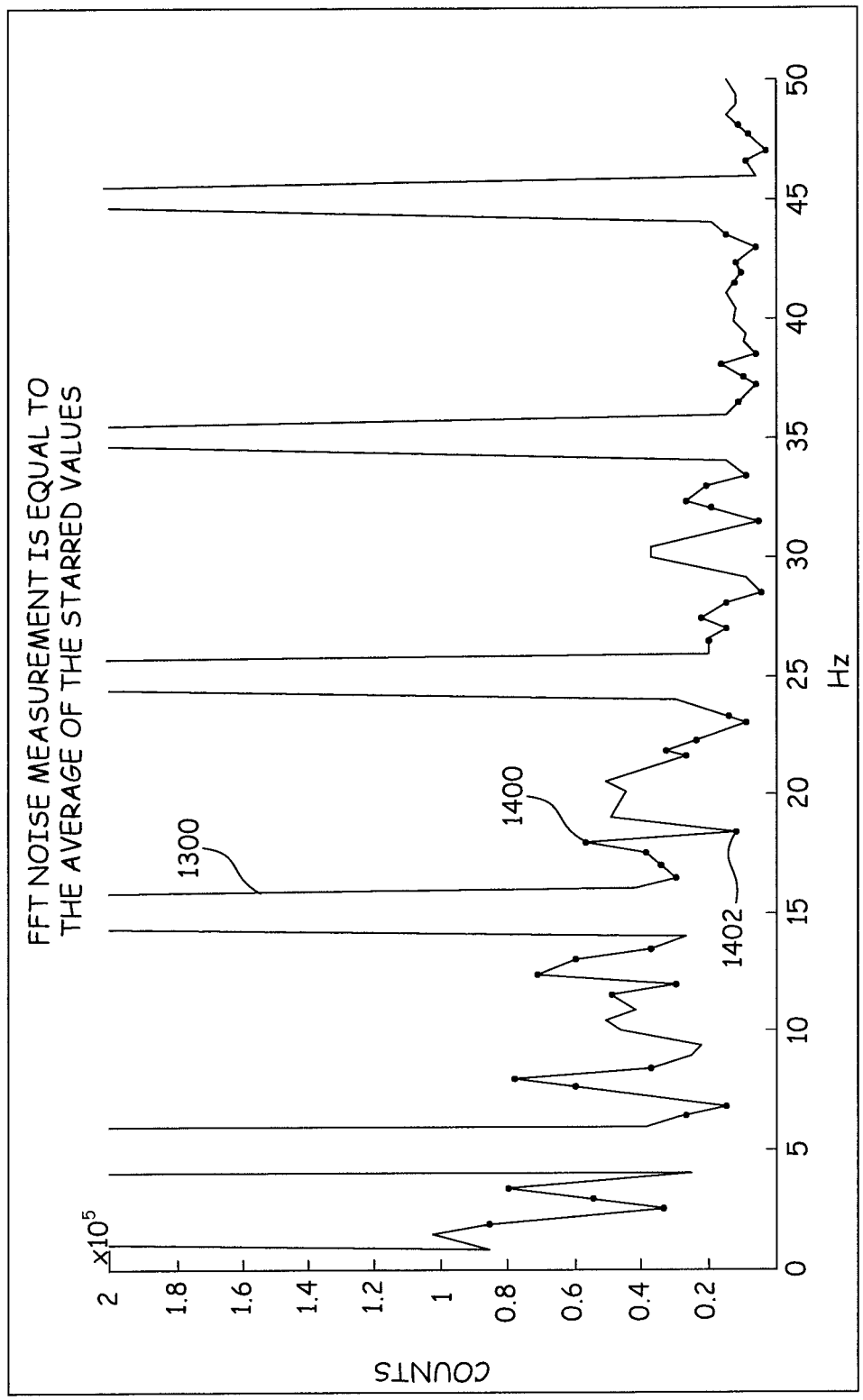
FIG. 14 is an expanded view of one of the graphs of FIG. 13 showing samples used to determine a noise level in the magnetic flow meter sensor signal.

To simplify identifying the contaminant's contribution to the sensor signal, the magnitudes of the signal at harmonic frequencies of the drive frequency are ignored since those frequencies include large magnitudes due to the response of the liquid to the magnetic field. For example, FIG. 14 shows an expanded view of graph 1300 with dots positioned at each frequency that is used in the noise determination. In graph 1300, the drive frequency is 5 Hz and values at even and odd multiples of this frequency are not used to determine the noise level. Thus, at 10, 20, 30, and 40 Hz, dots are not present on graph 1300. (Note that in FIG. 14 the magnitude of the frequency-domain signal at the odd multiples exceeds the scale of the drawing, but if the magnitudes could be seen there would be no dots and no values taken at 5, 15, 25, 35, and 45 Hz.)

Figure 15:
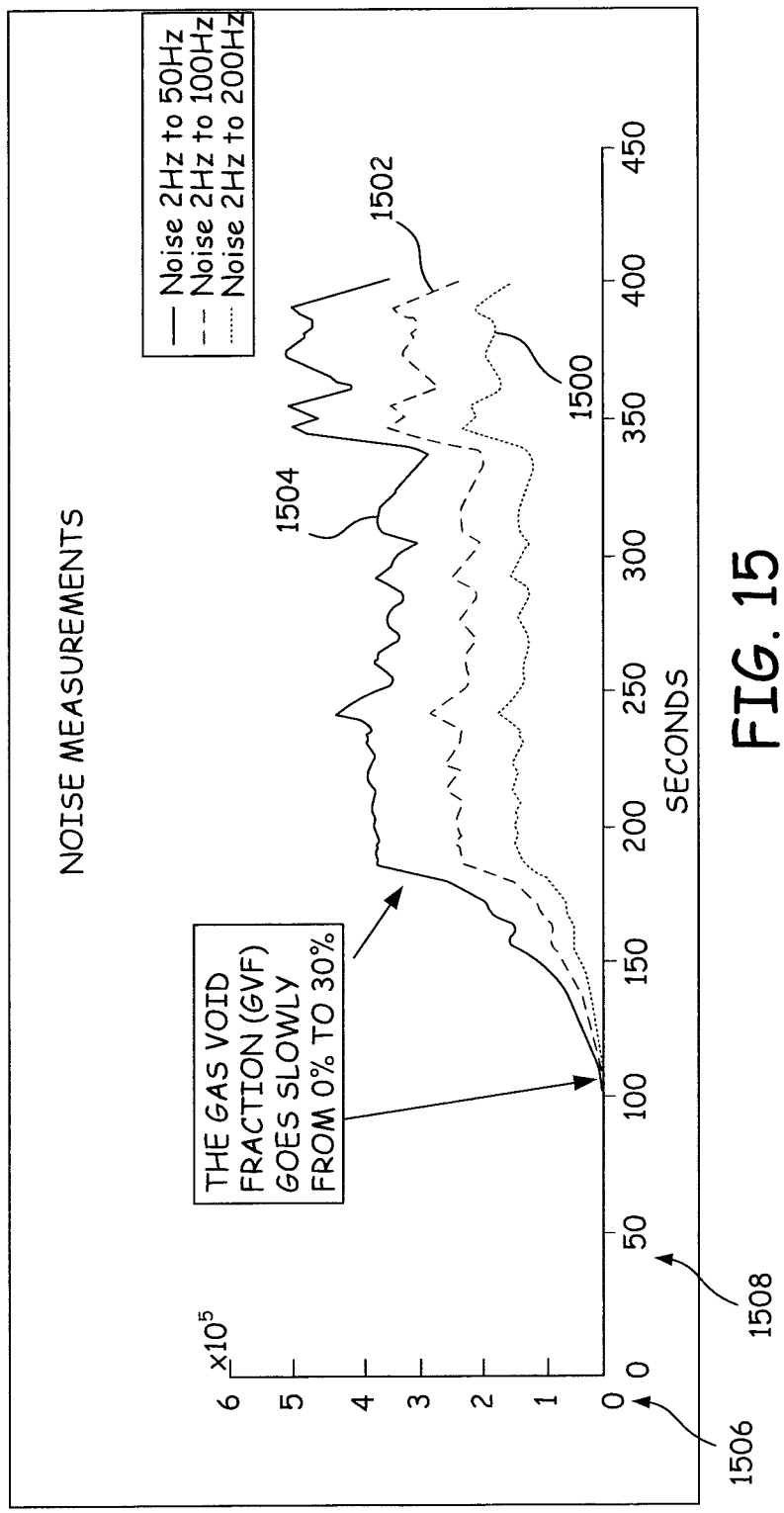
FIG. 15 are graphs of noise levels in magnetic flow meter sensor signals determined for different ranges of frequencies during an increase in gas void fractions.

In general, the noise is distributed across many frequencies as indicated by the graphs of FIG. 15 where three separate graphs 1500, 1502, and 1504 of noise versus time are shown for an increase in gas void fraction from zero to thirty percent using three respective frequency bands: 2-50 Hz, 2-100 Hz, and 2-200 Hz. In FIG. 15, the magnitude of the noise is shown along vertical axis 1506 and time is shown along horizontal axis 1508. For each frequency band, the noise level increases as the amount of gas in the liquid increases. In addition, the noise level is seen to increase more for the wider band of frequencies 1504 than for the narrower band of frequencies 1500, indicating that the noise is distributed across a wide spectrum of frequencies. For the 2-200 Hz frequency band, the noise level is shown to increase 175 times for a 30% increase in gas void fraction.

Figure 16:
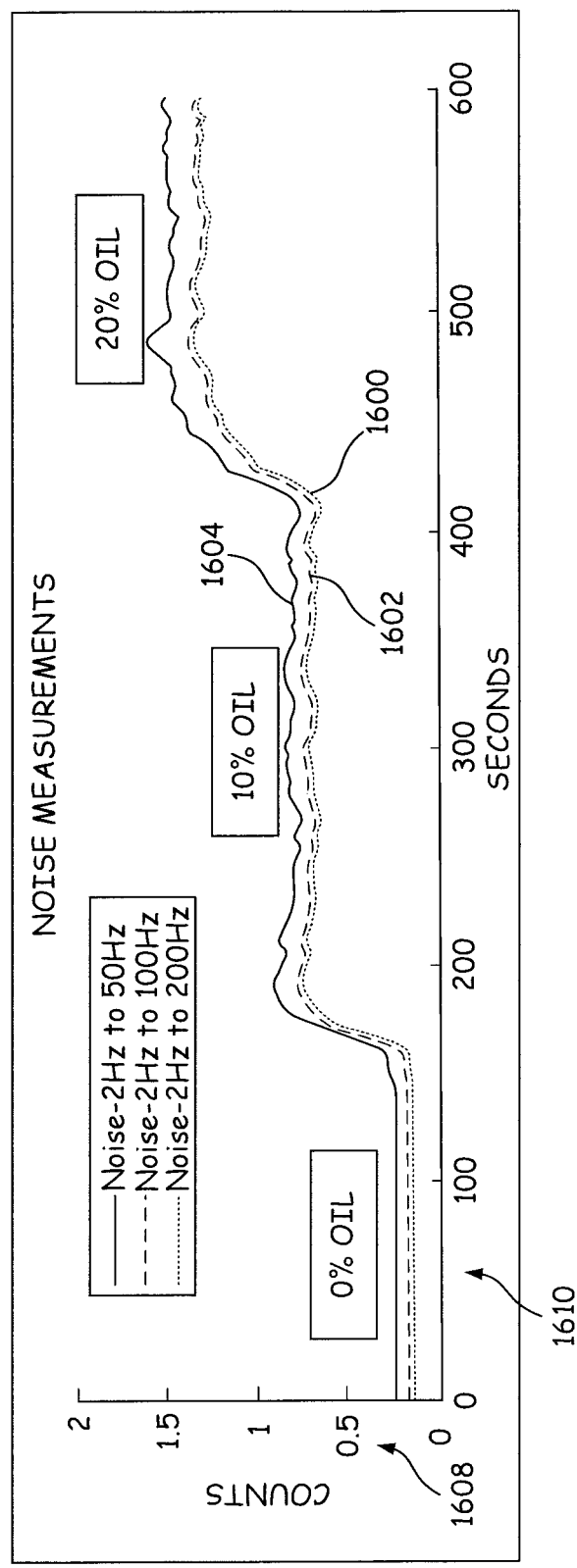
FIG. 16 are graphs of noise levels in magnetic flow meter sensor signals determined for different ranges of frequencies during an increase in oil percentage in a water line.

Similarly, in FIG. 16, three graphs 1600, 1602 and 1604 of noise versus time show an increase in noise as the percentage of oil in a water line is increased from zero to ten percent and then to twenty percent for respective frequency bands of 2-50 Hz, 2-100 Hz, and 2-200 Hz. In FIG. 16, the magnitude of the noise is shown along vertical axis 1608 and time is shown along horizontal axis 1610. As shown in FIG. 16, the noise increases with each increase in the percentage of oil in the water line for each frequency band.

Figure 17:
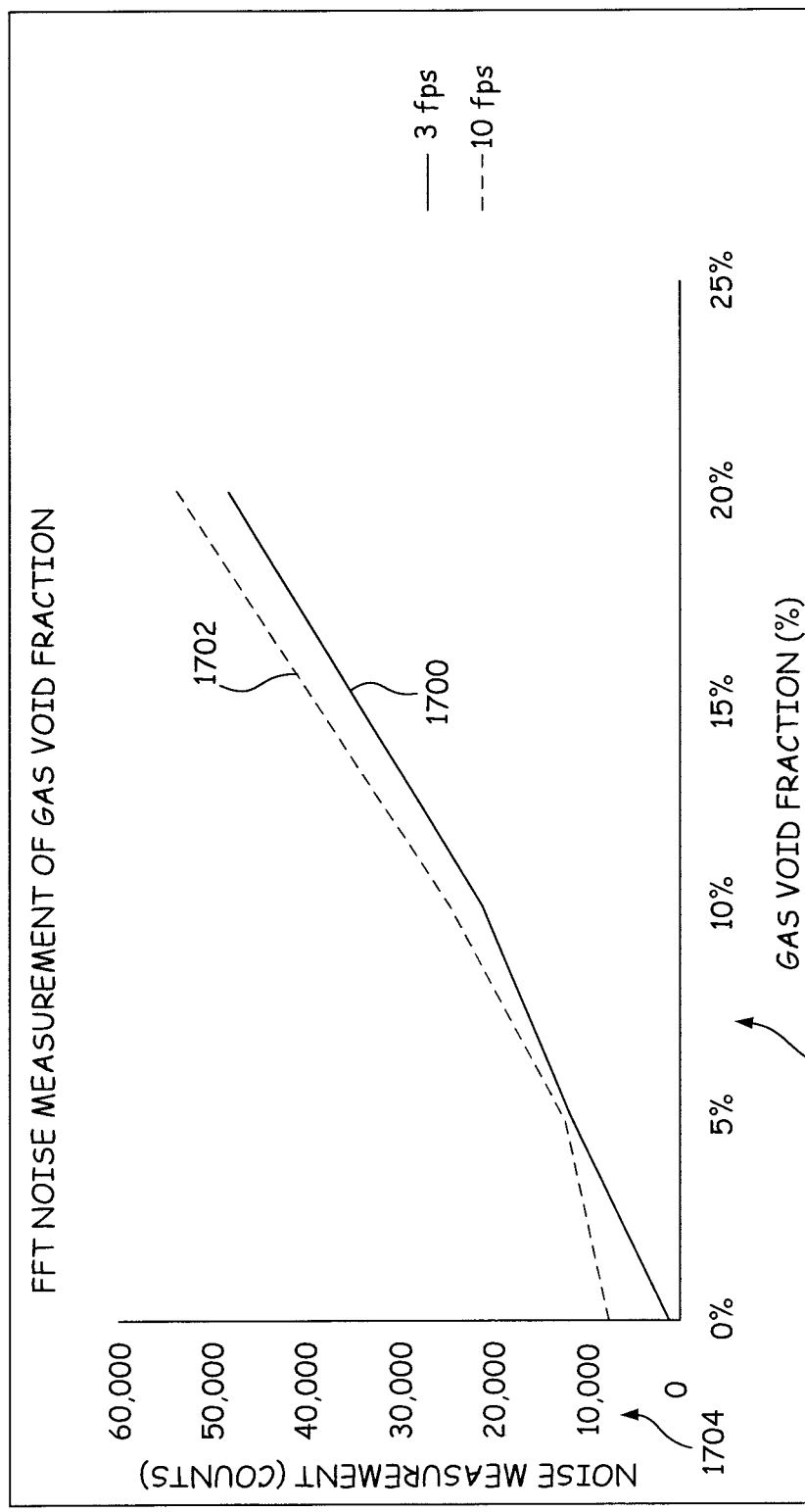
FIG. 17 shows graphs of noise levels in magnetic flow meter sensor signals as a function of gas void fractions for two separate flow rates.

The relationship between the frequency-domain determined noise level and the gas void fraction in the liquid has also been found by the inventors to be independent of the flow rate of the liquid. For example, in FIG. 17 two graphs 1700 and 1702 are shown for two respective flow rates of three feet per second and ten feet per second. Graphs 1700 and 1702 show the relationship between noise on vertical axis 1704 and gas void fraction on horizontal axis 1706. As shown in FIG. 17, graphs 1700 and 1702 have similar slopes and intercepts, which indicates that the relationship between noise and gas void fraction is independent of flow rate.

Figure 18:
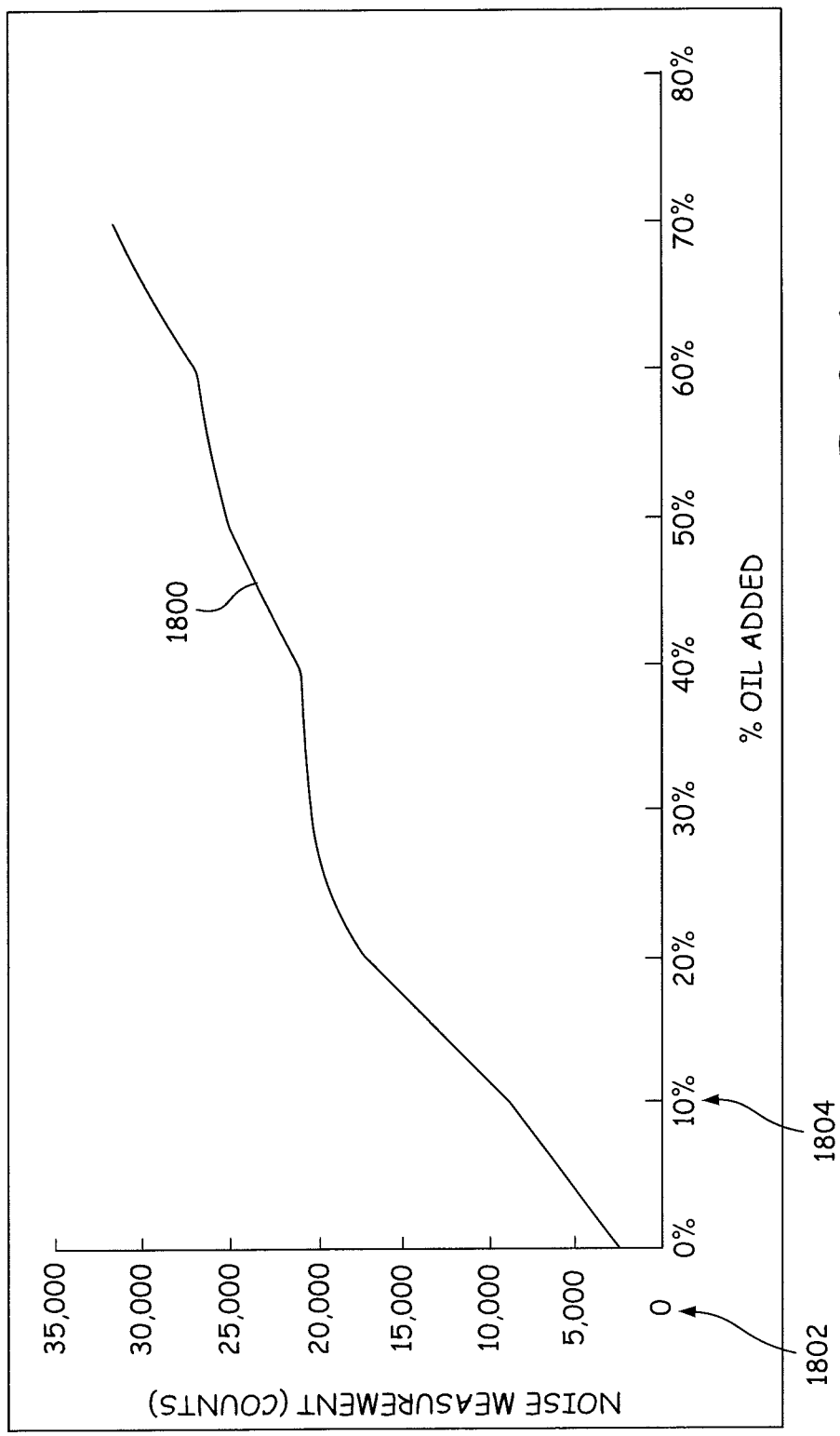
FIG. 18 shows a graph of noise levels in magnetic flow meter sensor signals as a function of oil levels in a water line.

FIG. 18 provides a graph 1800 showing a relationship between frequency-domain determined noise and a percentage of oil added to a water flow. In FIG. 18, the noise magnitude is shown along vertical axis 1802 and the oil percentage is shown along horizontal axis 1804. Graph 1800 indicates that the noise level generally increases as the percentage of oil in the water flow increases.

Figure 19:
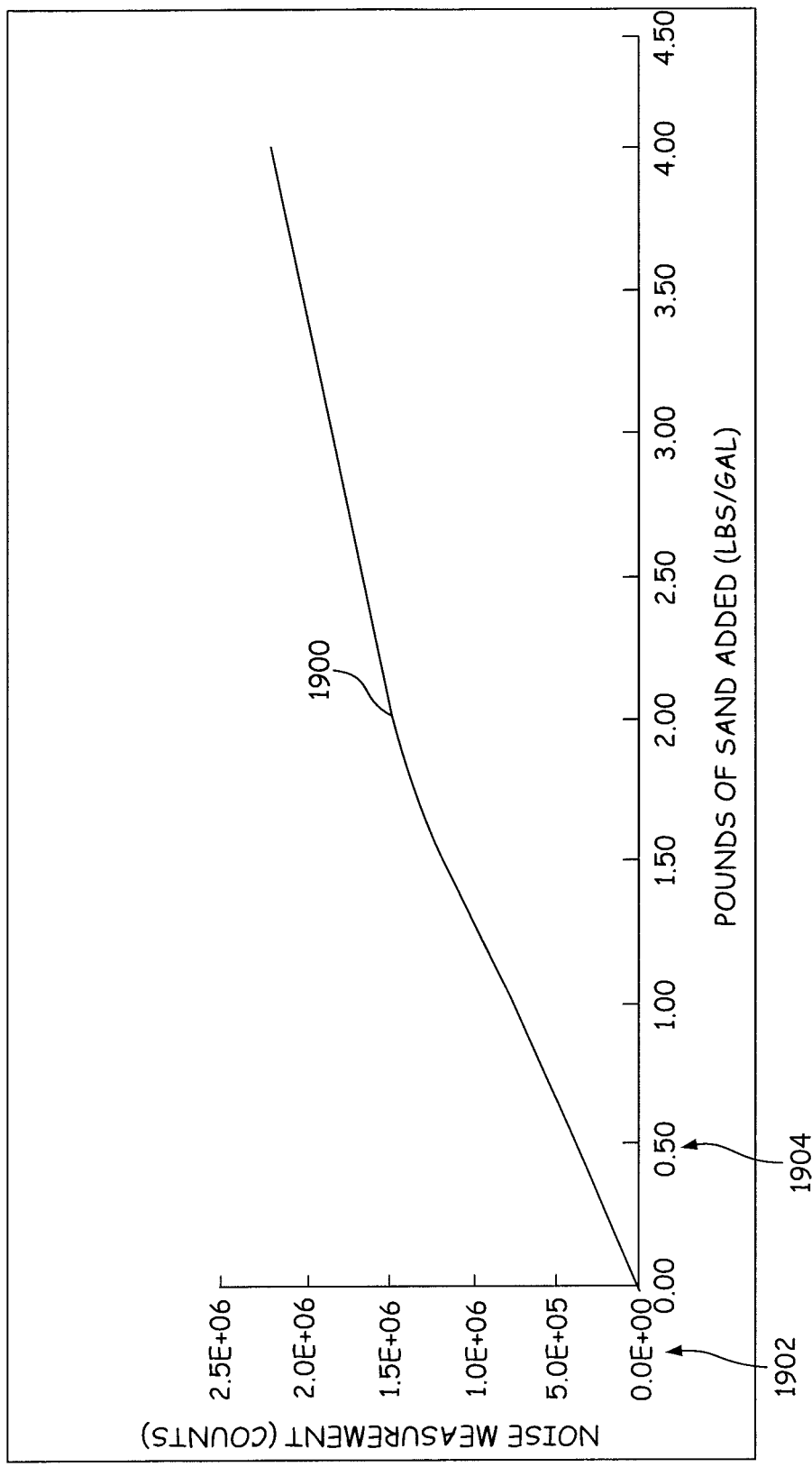
FIG. 19 shows a graph of noise levels in magnetic flow meter sensor signals as a function of pounds of sand in a water line.

FIG. 19 provides a graph 1900 showing the relationship between frequency-domain determined noise and pounds of sand in a water flow. In FIG. 19, the noise magnitude is shown along vertical axis 1902 and the amount of sand is shown along horizontal axis 1904. Graph 1900 indicates that the noise level increases as the amount of sand increases.

Figure 20:
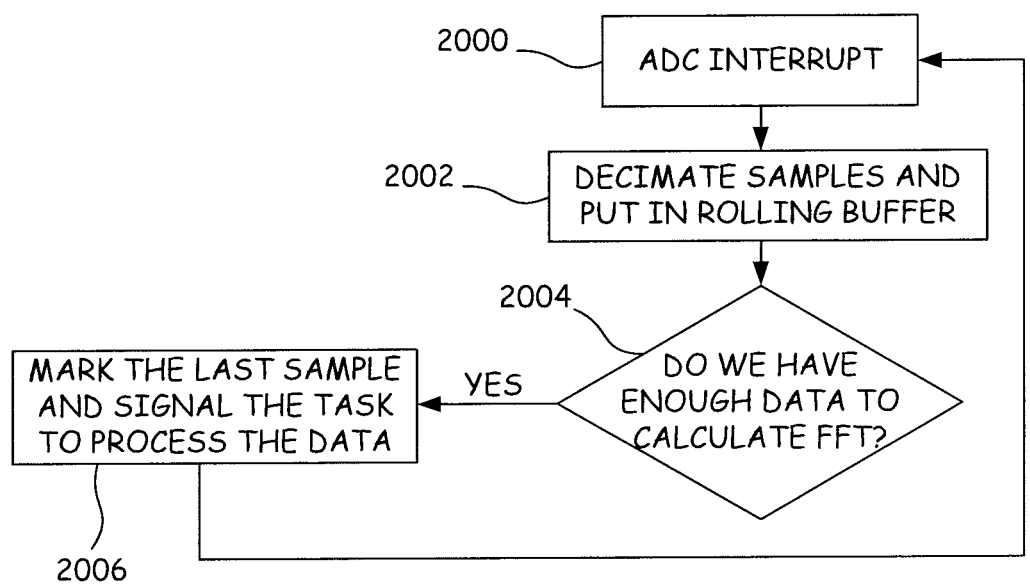
FIG. 20 is a flow diagram of a method of collecting noise data in accordance with a further embodiment.
Figure 21:
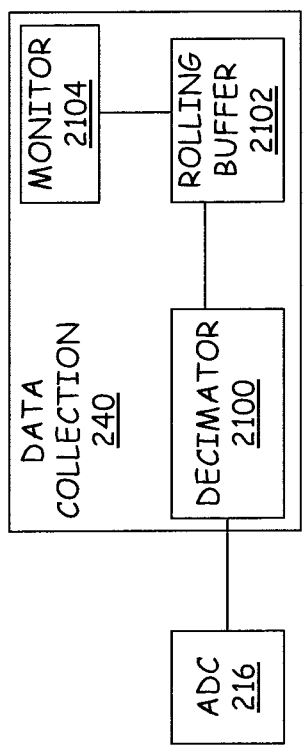
FIG. 21 is a block diagram of the elements used in the method of FIG. 20.

FIG. 20 provides a flow diagram of a method used by data collection module 240 to collect data for performing frequency-domain noise level identification. FIG. 21 provides a block diagram of elements used in the method of FIG. 20.

At step 2000, analog-to-digital convertor 216 issues an interrupt indicating that a new digital sample has been produced from the magnetic flow meter sensor signal. In response, at step 2002, a decimator 2100 applies a decimation algorithm to the sample to determine if the sample should be stored in a rolling buffer 2102. The decimating algorithm selects a subset of the samples for storage in rolling buffer 2102 thereby acting as a low pass digital filter. At step 2004, a monitor 2104 determines if enough samples have been added to rolling buffer 2102 to support a Fast Fourier Transform. If more samples are needed, the process of FIG. 20 returns to step 2000 to wait for another interrupt from analog-to-digital convertor 216. If rolling buffer 2102 contains enough samples for the Fast Fourier Transform, the location of the last sample placed in rolling buffer 2102 is recorded and the noise identification module 242 is signaled to begin the noise identification task at step 2006. After step 2006, the process returns to step 2000 to wait for the next interrupt from analog-to-digital convertor 216.

Figure 23:
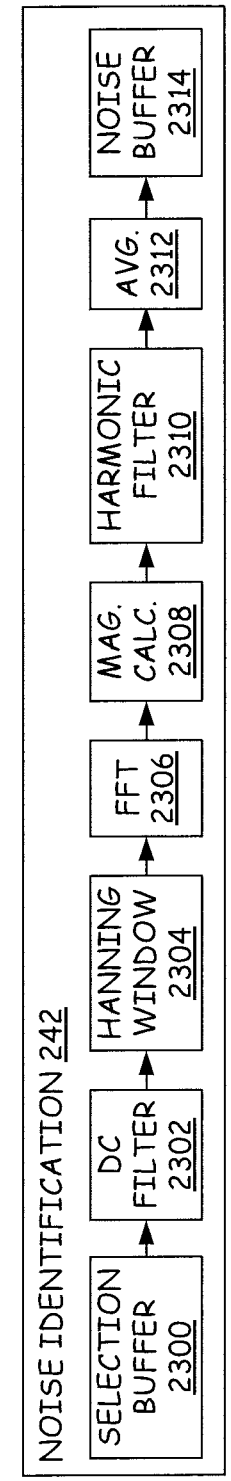
FIG. 23 is a block diagram of elements used in the method of FIG. 22.
Figure 22:
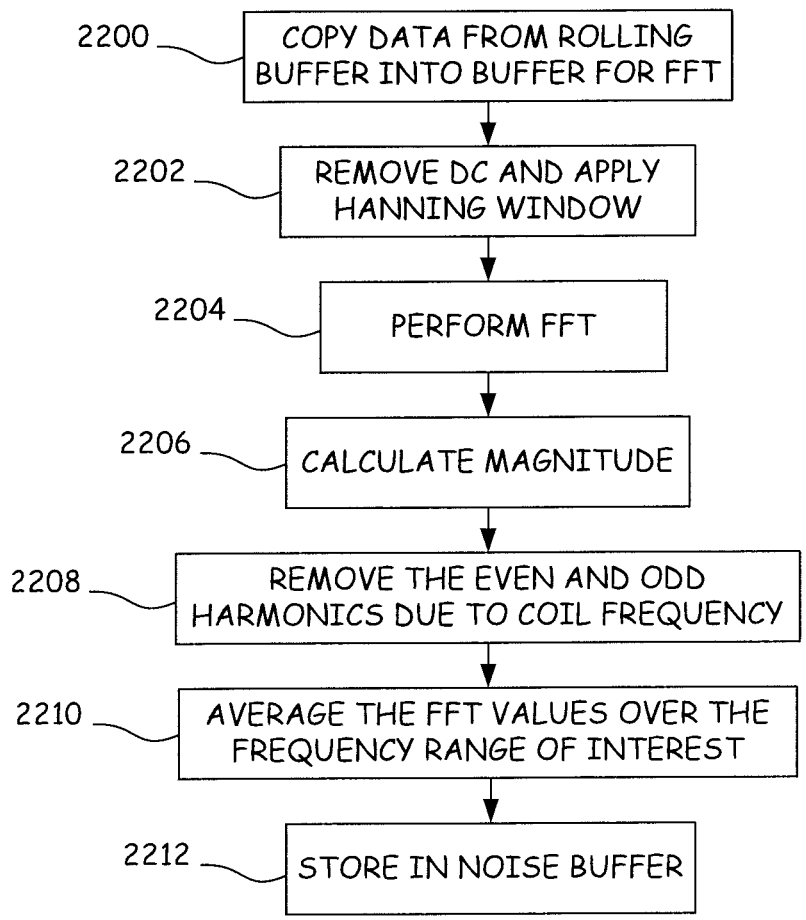
FIG. 22 is a flow diagram of a method of identifying noise levels in a magnetic flow meter sensor signal in accordance with a further embodiment.

FIG. 22 provides a flow diagram of a method performed by noise identification module 242 to identify the noise in the sensor signal using a frequency-domain technique. FIG. 23 provides a block diagram of elements used in the method of FIG. 22.

At step 2200, the start and end locations of the next set of data in rolling buffer 2102 to be processed are used to copy the data from rolling buffer 2102 to a selection buffer 2300. By copying these values, step 2200 is selecting a section or part of the sensor signal for conversion into the frequency domain. At step 2202, the data in selection buffer 2300 is applied to a DC filter 2302, which removes the DC component from each value of the data. In accordance with one embodiment, the DC component is simply an average of all of the data in selection buffer 2300. After the DC component has been removed from the data, the data are applied to a Hanning window 2304, which reduces the magnitudes of the data at the beginning and the end of the current section of the sensor signal to reduce frequency leakage when the Fast Fourier Transform is applied. At step 2204, the resulting data values are applied to a Fast Fourier Transform 2306, which converts the time-domain data values into a set of frequency-domain data values, with each frequency-domain data value being a complex number representing the magnitude and phase of the sensor signal for a respective frequency. At step 2206, each complex number is applied to a magnitude calculator 2308 to determine the magnitude for each frequency. At step 2208, the magnitudes are applied to a harmonic filter 2310, which removes the magnitudes for frequencies that are even or odd harmonics of the coil drive frequency. Such harmonic frequencies contain the liquid's response to the drive signal as well as the noise in the signal due to a contaminant in the liquid. By removing the magnitudes for the harmonic frequencies, the noise due to a contaminant can be isolated from the remainder of the sensor signal. At step 2210, the filtered magnitudes are averaged by an average calculator 2312 and the average is stored in a noise buffer 2314 for the section of the sensor signal selected in step 2200.

The noise values in noise buffer 2314 are then applied to a contaminant identification module 244 in the same manner as discussed above for the time-domain noise values. In particular, the method of FIG. 11 and the block diagram of FIG. 12 can be used for the frequency-domain based noise values in the same way that they were used for the time-domain based noise values.

The various modules and functional blocks discussed above can be implemented as dedicated circuits, microcontrollers executing instructions written into one or more RAM or ROM devices within process transmitter 200 or one or more microprocessors executing instructions stored in one or more RAM or ROM devices within process transmitter 200.

In accordance with a further embodiment, the noise in the magnetic flow meter sensor signal can additionally be used to detect valve chatter. During valve chatter, a relief valve in separator 100 rapidly opens and closes causing rapid fluctuations in the pressure within separator 100. This pressure fluctuation produces a corresponding fluctuation in the speed of the flow through conduits 140 and 146. Such fluctuations in the speed of the flow appear as noise in the magnetic flow meter sensor signal. As such, isolating and measuring the noise in the sensor signal using either of the embodiments discussed above allows the valve chatter to be detected since the noise level of the sensor signal will increase dramatically during valve chatter.

Although the present invention has been described with reference to preferred embodiments, workers skilled in the art will recognize that changes may be made in form and detail without departing from the spirit and scope of the invention.

What is claimed is:

1. A magnetic flow meter comprising:
   electrode sensors generating a sensor signal indicative of flow of a conductive liquid through a conduit;
   a noise identification module identifying a noise level in the sensor signal;
   a contaminant identification module using the noise level to determine whether a contaminant is in the conductive liquid in the conduit,
   wherein:
      the noise identification module identifies the noise level in a frequency-domain representation of the sensor signal; and
      the frequency-domain representation of the sensor signal is a filtered representation, in which harmonics of a frequency of a drive signal used to generate a magnetic field in the conduit have been filtered.

2. The magnetic flow meter of claim 1 wherein the sensor signal comprises a periodic square wave and the magnetic flow meter further comprises a data collection module that selects samples of the sensor signal by limiting the selected samples to samples that occur at an end portion of each half-cycle of the square wave.

3. The magnetic flow meter of claim 1, wherein:
   the sensor signal comprises a multi-step pulsed DC wave having a first frequency square wave superimposed on a second frequency square wave;
   the first frequency is higher than the second frequency; and
   the magnetic flow meter further comprises a data collection module that selects samples of the sensor signal by limiting the selected samples to samples that occur at an end portion of each half-cycle of the first frequency square wave.

4. The magnetic flow meter of claim 1 wherein the sensor signal comprises a sine wave and the magnetic flow meter further comprises a data collection module that applies samples of the sensor signal to a high pass filter.

5. The magnetic flow meter of claim 1 wherein the noise identification module identifies a plurality of noise levels.

6. The magnetic flow meter of claim 5 wherein the contaminant identification module further comprises a filter that filters the plurality of noise levels to produce a filtered noise level and wherein the contaminant identification module uses the filtered noise levels to determine whether a contaminant is in the conductive liquid.

7. The magnetic flow meter of claim 1 wherein a portion of the noise level is due to a gas contaminant.

8. The magnetic flow meter of claim 7 wherein the conductive liquid is water.

9. The magnetic flow meter of claim 1 wherein the conductive liquid is water and a portion of the noise level is due to an oil contaminant.

10. The magnetic flow meter of claim 1 wherein a portion of the noise level is due to a solid contaminant.

11. The magnetic flow meter of claim 1, wherein harmonics of line noise frequencies are filtered in the frequency-domain representation of the sensor signal.

12. A method comprising:
applying a drive signal to generate a magnetic field in a conduit carrying a conductive liquid;
receiving a sensor signal from electrodes positioned along the conduit;
converting the sensor signal to a frequency-domain representation;
filtering the frequency-domain representation including filtering values for frequencies that are harmonics of a frequency of the drive signal using a filter;
determining a noise level in the filtered frequency-domain representation; and
determining whether the conductive liquid contains a contaminant using the noise level.

13. The method of claim 12 wherein determining the noise level comprises selecting samples of the sensor signal at the end of half-cycles in the sensor signal and using the selected samples to determine the noise level.

14. The method of claim 13 wherein determining the noise level further comprises determining a difference between a maximum and a minimum of the selected samples.

15. The method of claim 12 wherein determining the noise level comprises determining separate noise levels for each of a plurality of sections of the sensor signal to form a plurality of noise levels and filtering the plurality of noise levels.

16. The method of claim 12 wherein determining whether the conductive liquid contains a contaminant comprises determining whether the conductive liquid contains a gas.

17. The method of claim 12 wherein determining whether the conductive liquid contains a contaminant comprises determining whether the conductive liquid contains an oil.

18. The method of claim 12 wherein determining whether the conductive liquid contains a contaminant comprises determining whether the conductive liquid contains a solid particulate.

19. The method of claim 12, wherein filtering the frequency-domain representation includes filtering values for frequencies that are harmonics of line noise frequencies.

20. A process transmitter comprising:
a magnetic coil;
electrode sensors configured to generate a sensor signal;
a noise identification module configured to convert a section of the sensor signal to a frequency-domain representation, filter the frequency-domain representation including filtering values associated with harmonics of a frequency of a drive signal applied to the magnetic coil, and determine a level of noise in the filtered frequency-domain representation; and
a contaminant identification module configured to identify that a conductive liquid contains a contaminant based on the determined level of noise.

21. The process transmitter of claim 20 wherein the noise identification module is further configured to select samples of the sensor signal to use to determine the level of noise in the sensor signal, wherein the selected samples exclude samples at the beginning of half-cycles of a period signal in the sensor signal.

22. The process transmitter of claim 20 wherein the contaminant comprises gas.

23. The process transmitter of claim 20 wherein the contaminant comprises oil.

24. The process transmitter of claim 20 wherein the contaminant comprises sand.

25. The process transmitter of claim 20, wherein the noise identification module is configured to filter the frequency-domain representation to filter values associated with harmonics of line noise frequencies.

26. A magnetic flow meter comprising:
electrode sensors generating a sensor signal indicative of flow of a conductive liquid through a conduit in a process system;
a noise identification module identifying a noise level in the sensor signal; and
a valve chatter identification module using the noise level to determine whether to issue an alert indicating valve chatter in the process system.

* * * * *